(12) United States Patent
Chen et al.

(10) Patent No.: US 12,053,536 B2
(45) Date of Patent: Aug. 6, 2024

(54) ORAL CARE COMPOSITIONS

(71) Applicant: Colgate-Palmolive Company, New York, NY (US)

(72) Inventors: Xiang Chen, Somerset, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 121 days.

(21) Appl. No.: 17/713,611

(22) Filed: Apr. 5, 2022

(65) Prior Publication Data
US 2022/0323319 A1    Oct. 13, 2022

Related U.S. Application Data

(60) Provisional application No. 63/172,159, filed on Apr. 8, 2021.

(51) Int. Cl.
| | |
|---|---|
| A61K 8/22 | (2006.01) |
| A61K 8/36 | (2006.01) |
| A61K 8/46 | (2006.01) |
| A61K 8/60 | (2006.01) |
| A61K 8/81 | (2006.01) |
| A61K 8/86 | (2006.01) |
| A61Q 11/00 | (2006.01) |

(52) U.S. Cl.
CPC .............. *A61K 8/22* (2013.01); *A61K 8/361* (2013.01); *A61K 8/463* (2013.01); *A61K 8/60* (2013.01); *A61K 8/8176* (2013.01); *A61K 8/86* (2013.01); *A61Q 11/00* (2013.01); *A61K 2800/30* (2013.01); *A61K 2800/31* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 2,124,971 A | 7/1938 | Eisenberg et al. | |
| 4,279,888 A | 7/1981 | Suganuma et al. | |
| 4,486,404 A * | 12/1984 | Weinert .................. | A61K 8/42 424/769 |
| 5,008,106 A | 4/1991 | Merianos et al. | |
| 5,122,370 A | 6/1992 | Merianos et al. | |
| 5,171,564 A | 12/1992 | Nathoo et al. | |
| 5,776,435 A | 7/1998 | Gaffar et al. | |
| 5,945,032 A | 8/1999 | Breitenbach et al. | |
| 6,540,971 B2 | 4/2003 | Gam | |
| 7,025,950 B2 | 4/2006 | Majeti et al. | |
| 7,166,235 B2 | 1/2007 | Majeti et al. | |
| 8,211,409 B2 | 7/2012 | Baig et al. | |
| 8,540,971 B2 | 9/2013 | Zaidel et al. | |
| 8,591,868 B2 | 11/2013 | Chopra et al. | |
| 9,174,070 B2 | 11/2015 | Chopra et al. | |
| 9,271,904 B2 | 3/2016 | Gebreselassie et al. | |
| 9,370,472 B2 | 6/2016 | Fei et al. | |
| 9,498,425 B2 | 11/2016 | Chopra et al. | |
| 9,517,194 B2 | 12/2016 | Zaidel et al. | |
| 9,532,932 B2 | 1/2017 | Prencipe et al. | |
| 9,724,280 B2 | 8/2017 | Fei et al. | |
| 9,782,339 B2 | 10/2017 | Chopra et al. | |
| 9,883,995 B2 | 2/2018 | Prencipe et al. | |
| 9,895,304 B2 | 2/2018 | Zaidel et al. | |
| 9,901,521 B2 | 2/2018 | Porter-Maloney et al. | |
| 9,974,634 B2 | 5/2018 | Maloney et al. | |
| 9,999,585 B2 | 6/2018 | Fei et al. | |
| 10,052,270 B2 | 8/2018 | Prencipe et al. | |
| 10,092,468 B2 | 10/2018 | Hashimoto | |
| 10,149,804 B2 | 12/2018 | Fei et al. | |
| 10,363,210 B2 | 7/2019 | Chopra et al. | |
| 11,141,364 B2 | 10/2021 | Pan et al. | |
| 2004/0136928 A1 | 7/2004 | Holme et al. | |
| 2005/0036956 A1 | 2/2005 | Fei et al. | |
| 2005/0038181 A1 | 2/2005 | Chopra et al. | |
| 2006/0045854 A1 | 3/2006 | Zaidel et al. | |
| 2006/0062744 A1 | 3/2006 | Lokken | |
| 2006/0099155 A1 | 5/2006 | MacDonald et al. | |
| 2007/0071695 A1 | 3/2007 | Chopra et al. | |
| 2007/0071696 A1 | 3/2007 | Wang et al. | |
| 2013/0195942 A1 | 8/2013 | Prencipe et al. | |
| 2014/0377193 A1 | 12/2014 | Chopra et al. | |

(Continued)

FOREIGN PATENT DOCUMENTS

| | | |
|---|---|---|
| CA | 2484372 | 3/2006 |
| CA | 2830684 | 4/2007 |
| CA | 3134464 | 10/2020 |
| EP | 0868903 | 11/2006 |
| EP | 3086861 | 2/2019 |
| JP | 2007-518733 | 7/2007 |
| WO | 1991/007184 | 5/1991 |
| WO | 1997/011675 | 4/1997 |
| WO | 2007/037961 | 4/2007 |
| WO | 2014/092735 | 6/2014 |
| WO | 2014/092736 | 6/2014 |
| WO | 2015/084357 | 6/2015 |
| WO | 2019/108194 | 6/2019 |
| WO | 2019/108202 | 6/2019 |
| WO | 2019/117885 | 6/2019 |

OTHER PUBLICATIONS

Anonymous, 2005, "Tooth Whitener", Mintel Database GNPD AN: 394267.

(Continued)

*Primary Examiner* — Nannette Holloman

(57) ABSTRACT

Disclosed herein are oral care compositions comprising an oral care composition comprising a peroxide whitening complex present in an amount to provide from about 3.0% to about 8% of hydrogen peroxide by weight of the composition; a block copolymer of ethylene oxide and propylene oxide in an amount from about 0.01% to about 8% by weight of the composition; a stearate in an amount from about 0.3% to about 5% by weight of the composition; and a humectant in an amount from about 60% to about 90% by weight of the composition. Methods of making and using the oral care compositions are also provided.

20 Claims, No Drawings

(56) References Cited

U.S. PATENT DOCUMENTS

2017/0049671 A1 2/2017 Prencipe et al.
2020/0405753 A1 12/2020 Daep et al.
2021/0236400 A1* 8/2021 Kim .................. A61K 8/737

OTHER PUBLICATIONS

International Search Report and the Written Opinion of the International Searching Authority issued in International Application PCT/US2022/023421 mailed Jul. 21, 2022.
Ashland Specialty Chemical, "Peroxydone XL-10 Technical Datasheet," 2016, Retrieved from the Internet: http://cosmetics.specialchem.com/product/i-ashalnd-specialty-chemical-peroxydone-xl-10, Retrieved on Feb. 18, 2016.
Ashland, "Polyplasdone Crospovidone Superdisintegrants Product Overview," 2013, Retrieved from the Internet. http://www.ashland.com/Ashland/Static/Documents/ASI/PC11319_Polyplasdone_Overview.pdf, Retrieved on Feb. 18, 2016, pp. 1-4.
http://www.newdruginfo.com/pharmacopeia/usp28/v28230/usp28nf23s0_m66210.htm (Year: 2008).
International Search Report in International Application No. PCT/US11/038874, mailed Apr. 12, 2012, pp. 1-4.
International Search Report and Written Opinion of the International Searching Authority in International Application No. PCT/US2021/058202, mailed Feb. 24, 2022.
International Specialty Products (ISP), 2009, Peroxydone XL-10F, Product Sales Specifications, p. 1.
International Specialty Products, Inc. (ISP), 2004, Peroxydone XL-10C, Tentative Sales Specifications, p. 1.
Storehagen, Silje et al., 2003, Dentifrices and Mouthwashes Ingredients and Their Use, University of Oslo, pp. 1-49.
Written Opinion of the International Searching Authority in International Application No. PCT/US11/038874, mailed Dec. 12, 2012, pp. 1-7.

* cited by examiner

ORAL CARE COMPOSITIONS

CROSS-REFERENCE TO RELATED APPLICATION

This application claims the benefit of priority from U.S. Provisional Application No. 63/172,159, filed Apr. 8, 2021, the contents of which are hereby incorporated herein by reference in their entirety.

BACKGROUND

Conventional oral care products (e.g., toothpastes, gels, mouth rinse, etc.) containing whitening agents are often utilized to whiten teeth. For example, conventional toothpastes containing peroxides (e.g., hydrogen peroxide) are often utilized to oxidize chromophores either bound to surfaces of teeth, or accumulated beneath the teeth surface, to thereby whiten the teeth. However, peroxide compounds are highly reactive, and consequently difficult to formulate. Moreover, hydrogen peroxide can spontaneously decompose to form oxygen gas ($O_2$) and water, so that on storage, the dentifrice container may bloat, burst or leak, and the remaining formulation will not have enough peroxide remaining to clean and whiten teeth effectively. Some dentifrices initially comprise very high levels of peroxide, which decomposes over time, so that the exact amount of peroxide delivered on application is variable and largely depends on how long and under what conditions the dentifrice has been stored.

The peroxide may be present as hydrogen peroxide or as a source of bound hydrogen peroxide. Sources of bound hydrogen peroxide include urea peroxide, calcium peroxide and sodium percarbonate. However, it has been a challenge to formulate stable whitening toothpaste compositions with a high amount of bound hydrogen peroxide (e.g., providing about 4% hydrogen peroxide).

There is a need for peroxide-containing whitening oral care compositions containing a high amount of peroxide, and particularly bound hydrogen peroxide, which exhibit improved whitening efficacy and stability.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The inventors have discovered that utilization of certain ingredients within an oral care composition provides for improved delivery of hydrogen peroxide active ingredients. Furthermore, such compositions may be combined with other active ingredients to deliver oral care health benefits in addition to whitening. Additionally, certain embodiments of the oral care compositions may provide enhanced amounts of peroxide, such as PVP-$H_2O_2$ complexes, while simultaneously maintaining a high level of stability.

The inventors recognized that commonly used humectants in toothpaste, such as propylene glycol, PEG, glycerin, sorbitol, interact with PVP-$H_2O_2$ complexes differently, resulting in different degree of the instability of peroxide. Among them propylene glycol is commonly used as the major carrier in formulations containing PVP-$H_2O_2$ complexes due to its least interaction with PVP-$H_2O_2$ complexes.

In one aspect, the invention provides an oral care composition comprising a peroxide whitening complex present in an amount to provide from about 3.0% to about 8.0% of hydrogen peroxide by weight of the composition a block copolymer of ethylene oxide and propylene oxide in an amount from about 0.01% to about 8.0% by weight of the composition; a stearate in an amount from about 0.3% to about 5.0% by weight of the composition; and a humectant (e.g., propylene glycol) in an amount from about 60% to about 90% by weight of the composition. In certain embodiments, the whitening complex comprises a crosslinked polyvinylpyrrolidone complexed with hydrogen peroxide (PVP-$H_2O_2$). In certain embodiments, the peroxide whitening complex is present in an amount to provide hydrogen peroxide in an amount of from about 3% to about 5%, or about 3.5% to about 4.5%, or about 3.8% to about 4.2%, or about 4%, by weight of the composition. In certain embodiments, the block copolymer of ethylene oxide and propylene oxide is present in an amount from about 5.0% to about 7.5% by weight of the composition. In certain embodiments, the stearate is present in an amount from about 0.3% to 0.8% by weight of the composition. In certain embodiments, the stearate is selected from one or more of sodium stearate, potassium stearate, and calcium stearate. In certain embodiments, the stearate is sodium stearate. In certain embodiments, the propylene glycol is present in an amount of from about 60% to about 80% by weight of the composition. In certain embodiments, the composition further comprises sucralose. In certain embodiments, the sucralose is present in an amount from about 0.01% to about 0.08% by weight of the composition. In certain embodiments, the composition further comprises sodium lauryl sulfate. In certain embodiments, the sodium lauryl sulfate is present in an amount from about 0.01% to about 2.0% by weight of the composition. In certain embodiments, the sodium lauryl sulfate is present in an amount from about 0.01% to about 1.0% by weight of the composition. In certain embodiments, the composition is free or substantially free of abrasive. In certain embodiments, the composition is free or substantially free of water.

In other embodiments, the invention is directed towards a method of whitening teeth, comprising applying an oral care composition according to any one of the preceding embodiments to the surface of the teeth.

In other certain embodiments, the invention is directed towards a method of whitening teeth, comprising mixing an oral care composition according to any one of compositions described herein with a toothpaste, and applying the mixed composition to the surface of the teeth. In certain embodiments, the mixing is performed at an oral care composition to toothpaste mass ratio of about 1:1 to about 1:4. In certain embodiments, the mixing is performed at an oral care composition to toothpaste mass ratio of about 1:3.

In other embodiments, the invention is directed towards an oral care composition consisting of a crosslinked polyvinylpyrrolidone complexed with hydrogen peroxide (PVP-$H_2O_2$) present in an amount to provide from about 3.0% to about 8.0% of hydrogen peroxide by weight of the composition; a block copolymer of ethylene oxide and propylene oxide in an amount from about 0.01% to about 8.0% by weight of the composition; stearate in an amount from about 0.3% to about 1.0% by weight of the composition; a humectant (e.g., propylene glycol) in an amount from about 60% to about 90% by weight of the composition; sodium lauryl sulfate present in an amount from about 0.01% to about 2.0% by weight of the composition; and sucralose present in an amount from about 0.01% to about 0.05% by weight of the composition. In certain embodiments, the invention is a method of whitening teeth, comprising applying the oral care composition described herein to the surface of the teeth.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other applications and methods. It is to be understood that the invention is not limited in its application to the details of any particular embodiment shown. The terminology used herein is for the purpose of description and not to limit the invention, its application, or uses.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", "containing", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight of the total composition. Reference to a molecule, or to molecules, being present at a "wt. %" refers to the amount of that molecule, or molecules, present in the composition based on the total weight of the composition.

According to the present application, use of the term "about" in conjunction with a numeral value refers to a value that may be +/−5% of that numeral. As used herein, the term "substantially free" is intended to mean an amount less than about 5.0 weight %, less than 3.0 weight %, 1.0 wt. %, less than about 0.5 wt. %, or less than about 0.25 wt. % of the composition.

As used herein, the term "effective amount" refers to an amount that is effective to elicit the desired biological response, including the amount of a composition that, when administered to a subject, is sufficient to achieve an effect toward the desired result. The effective amount may vary depending on the composition, the disease, and its severity and the age, weight, etc., of the subject to be treated. The effective amount can include a range of amounts. As is understood in the art, an effective amount may be in one or more doses, i.e., a single dose or multiple doses may be required to achieve the desired endpoint.

Unless defined otherwise, all technical and scientific terms used herein have the same meanings as commonly understood by one of ordinary skill in the art to which this invention belongs. All patents, patent applications, publications, and other references cited or referred to herein are incorporated by reference in their entireties for all purposes. In the event of a conflict in a definition in the present disclosure and that of a cited reference, the present disclosure controls.

The present disclosure is directed towards oral care whitening compositions containing a high level (e.g., up to about 4%, up to about 6%, up to about 8%, by weight of the composition) of hydrogen peroxide. It has been conventionally understood that formulating stable oral care compositions comprising an amount of PVP-$H_2O_2$ complexes of 3 wt. % or more has been challenging. PVP-$H_2O_2$ complex has a load limit in the amount of hydrogen peroxide the complex can carry. For example, the PVP-$H_2O_2$ complex (such as sold as Peroxydone™ XL-10, Ashland, USA) contains about 18% hydrogen peroxide. Thus, 22% Peroxydone™ XL-10 has to be added into an oral care composition to deliver about 4% hydrogen peroxide. However, the high level of crosslinked PVP present in 22% Peroxydone™ XL-10 thickens the formulation unacceptably over time, when in a propylene glycol based formulation. The present invention overcomes such problems, among others.

The invention provides, in an aspect, an oral care composition (Composition 1.0) comprising a peroxide whitening complex in an amount to provide from about 3.0% to about 8.0% of hydrogen peroxide by weight of the composition, a block copolymer of ethylene oxide and propylene oxide in an amount of from about 0.01% to about 8.0% by weight of the composition, a stearate in an amount from about 0.3% to about 5.0% by weight of the composition; and a humectant (e.g., propylene glycol) in an amount from about 60% to about 90% by weight of the composition.

In certain embodiments, the invention includes:
 1.1. Composition 1.0, wherein the whitening complex comprises or is a crosslinked polyvinylpyrrolidone complexed with hydrogen peroxide (PVP-$H_2O_2$).
 1.2. Composition 1.0 or 1.1, wherein the peroxide whitening complex is present in an amount to provide hydrogen peroxide in an amount of from about 3% to about 5%, or about 3.5% to about 4.5%, or about 3.8% to about 4.2%, or about 4% by weight of the composition.
 1.3. Any of preceding compositions, wherein the block copolymer of ethylene oxide and propylene oxide is present in an amount from about 5.0% to about 7.5% by weight of the composition.
 1.4. Any of preceding compositions, wherein the stearate is present in an amount from about 0.3% to 0.8% by weight of the composition.
 1.5. Composition 1.0 or 1.4, wherein the stearate is selected from one or more of sodium stearate, potassium stearate, and calcium stearate.
 1.6. Composition 1.5, wherein the stearate is sodium stearate.
 1.7. Any of preceding compositions, wherein the humectant (e.g., propylene glycol) is present in an amount of from about 60% to about 80% by weight of the composition.
 1.8. Any of preceding compositions, wherein the composition further comprises a sweetener safe for oral application selected from sucralose, saccharin, aspartame, acesulfame, or a combination thereof.

1.9. Composition 1.8, wherein the sucralose is present in an amount from about 0.01% to about 0.08% by weight of the composition.

1.10. Any of preceding compositions, wherein the composition further comprises sodium lauryl sulfate.

1.11. Composition 1.10, wherein the sodium lauryl sulfate is present in an amount from about 0.01% to about 2.0% by weight of the composition.

1.12. Composition 1.11, wherein the sodium lauryl sulfate is present in an amount from about 0.01% to about 1.0% by weight of the composition.

1.13. Any of preceding compositions, wherein the composition is free or substantially free of abrasive.

1.14. Any of preceding compositions, wherein the composition is free or substantially free of water.

In certain preferred embodiments, the invention includes a method (Method 1.0) of whitening teeth, comprising applying an oral care composition according to any one of Compositions 1.0 to 1.14 to the surface of the teeth.

In certain preferred embodiments, the invention includes a method (Method 2.0) of whitening teeth, comprising mixing an oral care composition according to any one of claims 1 to 15 with a toothpaste, and applying the mixed composition to the surface of the teeth. In certain embodiments of the Method 2.0, the mixing is performed at an oral care composition to toothpaste mass ratio of about 1:1 to about 1:4 (Method 2.1). In certain embodiments of the Method 2.0, the mixing is performed at an oral care composition to toothpaste mass ratio of about 1:3 (Method 2.2).

In certain preferred embodiments, the invention provides, in another aspect, an oral care composition (Composition 2.0) consisting of a crosslinked polyvinylpyrrolidone complexed with hydrogen peroxide ($PVP-H_2O_2$) present in an amount to provide from about 3.0% to about 8.0% of hydrogen peroxide, by weight of the oral care composition; a block copolymer of ethylene oxide and propylene oxide in an amount from about 0.01% to about 8.0%, by weight of the oral care composition; stearate in an amount from about 0.3% to about 5.0%, by weight of the oral care composition; propylene glycol in an amount from about 60% to about 90%, by weight of the oral care composition; sodium lauryl sulfate present in an amount from about 0.01% to about 2.0%, by weight of the oral care composition; and sucralose present in an amount from about 0.01% to 0.05%, by weight of the oral care composition.

In certain preferred embodiments, the invention provides a method (Method 3.0) of whitening teeth, comprising applying a composition 2.0 to the surface of the teeth.

The oral care composition of the present invention may be free or substantially free of water. For example, some embodiments contain water in an amount of less than 5.0 weight %, less than 3.0 weight %, less than 1.0 weight %, less than 0 1 weight %, less than 0.05 weight %, less than 0.01 weight %, less than 0 005 weight %, or less than 0.0001 weight %, based on a total weight of the oral care composition. In some embodiments, the oral care composition is anhydrous. In some embodiments, the oral care composition does not contain water.

The oral care composition of the present invention may be free or substantially free of abrasive. For instance, the oral care compositions may contain an abrasive(s) in an amount of less than 5.0 weight %, less than 3.0 weight %, less than 1.0 weight %, less than 0 1 weight %, less than 0.05 weight %, less than 0.01 weight %, less than 0.005 weight %, or less than 0.0001 weight %, based on a total weight of the oral care composition. In some embodiments, the oral care composition does not contain abrasive.

The oral care composition of the present invention may be a single phase oral care composition. For example, the peroxide whitening agent, the block copolymer of ethylene oxide and propylene oxide and all other ingredients of the composition may be maintained together with one another in a single phase and/or vessel. For example, the peroxide whitening agent, the block copolymer of ethylene oxide and propylene oxide and all other ingredients of the composition may be maintained together with one another in a single phase, such as a single homogenous phase. The single homogenous phase may be anhydrous.

The oral care composition may form at least a portion of or be used in one or more oral care products. For example, the oral care composition may form at least a portion of or be used with a toothpaste. In some embodiments, the oral care composition may typically be a gel of the toothpaste, or a whitening gel to be combined with the toothpaste. Thus, in some embodiments, the oral care products may comprise the oral care composition and a toothpaste. Additionally or alternatively, the oral care composition may include or be combined with an orally acceptable vehicle to form the oral care product. In some embodiments, the oral care composition is a toothpaste gel, or serum. In some embodiments, the oral care composition may be a serum or concentrate, and may be combined with an orally acceptable vehicle to form a final oral care product (e.g., toothpaste). In certain embodiments, the oral care composition, or serum, may include or be combined with an orally acceptable vehicle to form the oral care product (e.g., toothpaste). The oral care composition may comprise from about 5 wt. % to about 80 wt. % of the oral care product. For instance, the oral care product may comprise from about 5 wt. % to about 70 wt. %, about 5 wt. % to about 50 wt. %, about 5 wt. % to about 40 wt. %, about 5 wt. % to about 30 wt. %, about 5 wt. % to about 20 wt. %, or about 5 wt. % to about 10 wt. %; from about 15 wt. % to about 80 wt. %, about 15 wt. % to about 70 wt. %, about 15 wt. % to about 50 wt. %, about 15 wt. % to about 40 wt. %, about 15 wt. % to about 30 wt. %; about 25 wt. % to about 80 wt. %, about 25 wt. % to about 70 wt. %, about 25 wt. % to about 50 wt. %, about 25 wt. % to about 40 wt. %; about 35 wt. % to about 80 wt. %, about 35 wt. % to about 70 wt. %, about 35 wt. % to about 50 wt. %; about 45 wt. % to about 80 wt. %, about 45 wt. % to about 70 wt. %; about 55 wt. % to about 80 wt. %, about 55 wt. % to about 70 wt. %; about 65 wt. % to about 80 wt. %, or any ranges or subranges therebetween, of the oral care composition, optionally with the remainder being a dentifrice.

The amount of dentifrice in the oral care composition may, in some embodiments, be about 5 wt. % to about 70 wt. %, about 5 wt. % to about 50 wt. %, about 5 wt. % to about 40 wt. %, about 5 wt. % to about 30 wt. %, about 5 wt. % to about 20 wt. %, or about 5 wt. % to about 10 wt. %; from about 15 wt. % to about 80 wt. %, about 15 wt. % to about 70 wt. %, about 15 wt. % to about 50 wt. %, about 15 wt. % to about 40 wt. %, about 15 wt. % to about 30 wt. %; about 25 wt. % to about 80 wt. %, about 25 wt. % to about 70 wt. %, about 25 wt. % to about 50 wt. %, about 25 wt. % to about 40 wt. %; about 35 wt. % to about 80 wt. %, about 35 wt. % to about 70 wt. %, about 35 wt. % to about 50 wt. %; about 45 wt. % to about 80 wt. %, about 45 wt. % to about 70 wt. %; about 55 wt. % to about 80 wt. %, about 55 wt. % to about 70 wt. %; about 65 wt. % to about 80 wt. %, or any ranges or subranges therebetween, of the oral care composition, optionally with the remainder being an oral care composition.

Illustrative oral care products may include, but are not limited to, a toothpaste (dentifrice), a prophylactic paste, a tooth powder, a tooth polish, a tooth gel (e.g., whitening gel), a chewing gum, a lozenge, a mouthwash, a whitening strip, a paint-on gel, varnish, veneer, and/or the like. Additionally or alternatively, the oral care product may be a composition (e.g., a gel or paste) adapted for use with/in a tube, a syringe or a pump, or a dental tray comprising, or coated on an application support such as dental floss, interdental brush, dental pad, or a toothbrush (e.g., a manual, electric, sound, a combination thereof or ultrasound toothbrush). The oral care composition may be contained in any suitable container, such as a tube, bottle, jar, tub, or the like. The container may be comprised of or be formed of suitable materials, such as certain plastics or glass.

The oral care composition of the present invention comprises a peroxide whitening complex which acts as a source of bound hydrogen peroxide. The whitening complex may contain from about 10 to about 30% hydrogen peroxide, based on the weight of the whitening complex, e.g., about 15 to 25 wt. %, about 15 to 20 wt. %, or about 18 wt. %. Peroxide may be bound to a polymer such as PVP (polyvinylpyrrolidone). In some embodiments, the peroxide whitening complex is a crosslinked polyvinylpyrrolidone complexed with hydrogen peroxide (PVP-H$_2$O$_2$), e.g., Peroxydone™ XL-10 (Ashland Specialty Chemical). In some embodiments, the total amount of peroxide whitening complex provided delivers about 3.0 to about 8.0 wt. % of hydrogen peroxide based on the weight of the composition, e.g., about 3.5 to about 7.5 wt. %, about 3.5 to about 5.5 wt. %, or about 4 wt. %. In certain embodiments, the peroxide whitening complex may be present in an amount to provide from about 3% to about 8% of hydrogen peroxide by weight of the composition. In certain embodiments, the peroxide whitening complex is present in an amount to provide about 3.8% to about 4.2% by weight of the composition.

The oral care composition of the present invention typically comprises a block copolymer of ethylene oxide (EO) and propylene oxide (PO). The block copolymers of ethylene oxide and propylene oxide may be nonionic. For example, the block copolymers of ethylene oxide and propylene oxide may be a nonionic surfactant. The block copolymers of ethylene oxide and propylene oxide may be represented by formula (1).

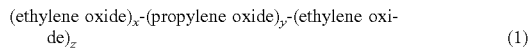

(ethylene oxide)$_x$-(propylene oxide)$_y$-(ethylene oxide)$_z$      (1)

where x may be an integer of from about 5 to about 15 (e.g., x=9-13, or about 11), y may be an integer from about 10 to about 20 (e.g., y=13-17, or about 16), and z may be an integer from about 5 to about 15 (e.g., x=9-13, or about 11). In a certain embodiment, the block copolymer of ethylene oxide and propylene oxide may be represented by formula (2).

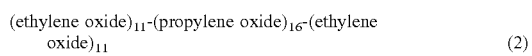

(ethylene oxide)$_{11}$-(propylene oxide)$_{16}$-(ethylene oxide)$_{11}$      (2)

The block copolymer of ethylene oxide and propylene oxide may have an average molecular weight of from about 1,000 Da to about 3,000 Da. For example, the block copolymer of ethylene oxide and propylene oxide may have an average molecular weight of from about 1,000 Da, about 1,100 Da, about 1,200 Da, about 1,300 Da, about 1,400 Da, about 1,500 Da, about 1,600 Da, about 1,700 Da, about 1,800 Da, or about 1,850 Da to about 1,950 Da, about 2,000 Da, about 2,100 Da, about 2,200 Da, about 2,300 Da, about 2,400 Da, about 2,500 Da, about 2,600 Da, about 2,700 Da, about 2,800 Da, about 2,900 Da, about 3,000 Da, or any range therebetween. In another example, the block copolymer of ethylene oxide and propylene oxide may have an average molecular weight of from about 1,000 Da to about 2,800 Da, about 1,100 Da to about 2,700 Da, about 1,200 Da to about 2,600 Da, about 1,300 Da to about 2,500 Da, about 1,400 Da to about 2,400 Da, about 1,500 Da to about 2,300 Da, about 1,600 Da to about 2,200 Da, about 1,700 Da to about 2,100 Da, about 1,800 Da to about 2,000 Da, or about 1,850 Da to about 1,950 Da, or any range therebetween. In some embodiments, the block copolymer of ethylene oxide and propylene oxide may have an average molecular weight of from about 1,850 Da to about 1,950 Da, e.g., about 1,900 Da.

Illustrative block copolymers of ethylene oxide (EO) and propylene oxide (PO) may be or include, but are not limited to, PLURONIC® L35, PLURONIC® LI, PLURONIC® L43, PLURONIC® L10, PLURONIC® L44, PLURONIC® 10R5, PLURONIC® 17R4, PLURONIC® L25R4, PLURONIC® P84, PLURONIC® P65, PLURONIC® PI 04, PLURONIC® PI 05, and the like, and combinations thereof, all of which are commercially available from BASF of Mount Olive, NJ. In a certain embodiment, the block copolymer of ethylene oxide and propylene oxide is PLURONIC® L35. Another illustrative ethylene oxide, propylene oxide block co-polymer is PLURACARE® L1220 (available from BASF, Wyandotte, Mich., United States of America).

The block copolymer of ethylene oxide and propylene oxide may be present in an amount of from about 0.01% to about 8% by weight of the composition. In some embodiments, the block copolymer of ethylene oxide and propylene oxide is present in an amount of from about 5% to about 7.5%, e.g., from about 6% to about 7.5%, or from about 6% to 7%, by weight of the composition.

The oral care composition of the invention may include a stearate. In certain embodiments, the stearate is selected from one or more of sodium stearate, potassium stearate, and calcium stearate. In certain embodiments, the stearate is sodium stearate. In other embodiments, the stearate is potassium stearate. The stearate may be present in an amount from about 0.01% to about 5%, by weight of the composition. In certain embodiments, the stearate is present in an amount from about 0.3% to about 5%, from about 0.3% to about 3%, from about 0.8% to about 5%, or from about 0.5% to about 3.5%, by weight of the composition. In certain embodiments, the stearate is present in an amount from about 0.3% to 0.8% by weight of the composition.

In some embodiment, the oral care composition of the present invention may have a viscosity of about 10,000 CPS to about 700,000 CPS, preferably about 30,000 CPS to about 300,000 CPS. As mentioned above, aspects of the invention are directed to oral care compositions that include propylene glycol and a PVP-H$_2$O$_2$ complex having a high concentration of hydrogen peroxide (e.g., 22 wt. % of hydrogen peroxide based on the weight of the PVP-H$_2$O$_2$ complex) without undergoing unsuitable thickening over time. For example, certain embodiments of the oral care composition comprise propylene glycol and a PVP-H$_2$O$_2$ complex having a high concentration of hydrogen peroxide of at least 10 wt. %, at least 15 wt. %, at least 20 wt. %, at least 22 wt. %, or at least 25 wt. %, based on the weight of the crosslinked PVP-H$_2$O$_2$ complex, wherein viscosity of the oral care composition does not increase by more than 20% (e.g., not more than 15%, or not more than 10%) over a 4 week period. The oral care composition of the present invention may comprise an additional surfactant other than the block copolymer of ethylene oxide and propylene oxide.

In some embodiments, the oral care composition may comprise an anionic surfactant. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylase, and sodium dodecyl benzenesulfonate. In some embodiments, the anionic surfactant is sodium lauryl sulfate (SLS). The anionic surfactant, e.g., sodium lauryl sulfate, may be present in an amount of from about 0.01 to about 5% by weight, about 0.01 to about 4% by weight, about 0.01 to about 3% by weight, about 0.01 to about 2% by weight, about 0.01 to about 1% by weight; from about 0.1 to about 5% by weight, about 0.1 to about 4% by weight, about 0.1 to about 3% by weight, about 0.1 to about 2% by weight, about 0.1 to about 1% by weight; from about 1 to about 5% by weight, about 1 to about 4% by weight, about 1 to about 3% by weight, about 1 to about 2% by weight; about 2 to about 5% by weight, about 2 to about 4% by weight, about 2 to about 3% by weight, or any range or subrange thereof, based on the total weight of the oral care composition. In at least one embodiment, the amount of anionic surfactant present in the oral care composition is in a range from 0.01% to 2% by weight, e.g., 0.05 to 1.5%, 0.8 to 2%, 0.8 th1.5%, or about 1%, by weight of the composition.

The oral care composition of the present invention may comprise fluoride, such as one or more fluoride ion sources (e.g., soluble fluoride salts). A wide variety of fluoride ion-yielding materials may be employed as sources of soluble fluoride. Illustrative fluoride ion sources include, but are not limited to, sodium fluoride, stannous fluoride, potassium fluoride, sodium monofluorophosphate, fluorosilicate salts, such as sodium fluorosilicate and ammonium fluorosilicate, amine fluoride, ammonium fluoride, and combinations thereof. In some embodiment, the fluoride ion source is sodium monofluorophosphate or sodium fluoride. The amount of the fluoride ion source present in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to supply 25 ppm to 5,000 ppm of fluoride ions, generally at least 500 ppm. e.g., 500 to 2000 ppm, e.g., 1000 ppm to 1600 ppm, e.g., 1450 ppm. In certain embodiments, the fluoride ion source is sodium monofluorophosphate and is present in an amount from about 0.01 to about 1.14%, by weight of the composition, including all values in between.

In certain preferred embodiments, the oral care composition utilizes humectant. Suitable humectants for use in the present invention include glycerin, sorbitol, glycol (s), xylitol, and other edible polyhydric alcohols. Non-limiting examples of glycols include ethylene glycol, propylene glycol, butylene glycol, hexylene glycol, pentylene glycol, diethylene glycol, dipropylene glycol, 1.3 propanediol, and glycerin. In some embodiments, the oral care composition includes one or more glycol(s) selected from polyethylene glycol, propylene glycol, and a combination thereof. In certain embodiments, the humectant is selected from glycerin, sorbitol, polyethylene glycol, propylene glycol, xylitol, or combinations thereof. In certain embodiments, humectants are selected from a polyhydric alcohol, which includes, but is not limited to glycerin, glycol, inositol, maltitol, mannitol, sorbitol, xylitol, propylene glycol, polypropylene glycol (PPG), polyethylene glycol (PEG) and mixtures thereof, or a saccharide, which includes, but is not limited to fructose, glucose, sucrose and mixtures of saccharides (e.g. honey), and combinations of two or more thereof. The oral care compositions of the present invention may comprise humectants in an amount of from about 0% to about 90%, from about 1% to about 25%, or from about 50% to about 85%, by weight of the oral care composition.

In certain preferred embodiments, the composition utilizes propylene glycol. The propylene glycol may be present at various amounts and concentrations. For example, the propylene glycol may be present in the oral care composition in an amount from about 20 to about 90 wt. %, about 20 to about 80 wt. %, about 20 to about 70 wt. %, about 20 to about 60 wt. %, about 20 to about 50 wt. %, about 20 to about 40 wt. %; about 10 to about 90 wt. %, about 10 to about 80 wt. %, about 10 to about 70 wt. %, about 10 to about 60 wt. %, about 10 to about 50 wt. %, about 10 to about 40 wt. %; about 20 to about 90 wt. %, about 20 to about 80 wt. %, about 20 to about 70 wt. %, about 20 to about 60 wt. %, about 20 to about 50 wt. %, about 20 to about 40 wt. %; about 30 to about 99 wt. %, about 30 to about 95 wt. %, about 30 to about 90 wt. %, about 30 to about 80 wt. %, about 30 to about 70 wt. %, about 30 to about 60 wt. %, about 30 to about 50 wt. %, about 30 to about 40 wt. %; about 40 to about 99 wt. %, about 40 to about 95 wt. %, about 40 to about 90 wt. %, about 40 to about 80 wt. %, about 40 to about 70 wt. %, about 40 to about 60 wt. %, about 40 to about 50 wt. %; about 50 to about 99 wt. %, about 50 to about 95 wt. %, about 50 to about 90 wt. %, about 50 to about 80 wt. %, about 50 to about 70 wt. %, about 50 to about 60 wt. %; about 60 to about 99 wt. %, about 60 to about 95 wt. %, about 60 to about 90 wt. %, about 60 to about 80 wt. %, about 60 to about 70 wt. %; about 70 to about 99 wt. %, about 70 to about 95 wt. %, about 70 to about 90 wt. %, about 70 to about 80 wt. %; about 80 to about 99 wt. %, about 80 to about 95 wt. %, about 80 to about 90 wt. %; about 90 to about 99 wt. %, about 90 to about 95 wt. %; or about 95 to about 99 wt. %, including ranges and subranges therebetween, based on the total weight of the oral care composition. In certain embodiments, propylene glycol is present from about 60% to about 90%, e.g., 60 to 80%, 70 to 90%, 60 to 75%, or about 70%, by weight of the oral care composition.

The oral care composition of the present invention may comprise a water-soluble nitrate salt. In certain embodiments, the water-soluble nitrate salt is selected from an alkali or alkaline earth metal nitrate, or zinc nitrate, silver nitrate, or ammonium nitrate. In certain embodiments, the water-soluble nitrate salt is an alkali metal nitrate salt or an alkaline earth metal nitrate salt. In certain embodiments, the nitrate salt is selected from lithium nitrate, sodium nitrate, potassium nitrate, magnesium nitrate, and calcium nitrate. In certain preferred embodiments, the nitrate salt is potassium nitrate. In certain embodiments, the water-soluble nitrate salt is present from about 0.01% to about 5.0%, e.g., 0.01-4.5%, 2.0-5.0%, 1.0-4.0%, or about 3.5%, by weight of the composition.

The oral care composition of the present invention may comprise anticalculus agents. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates, and phytate acid or its alkaline salt. In some embodiments, the anticalculus agent comprises tetrasodium pyrophosphate (TSPP), sodium tripolyphosphate (STPP), or a combination thereof.

The oral care composition of the present invention may comprise sodium acid pyrophosphate ($Na_2H_2P_2O_7$). In some embodiments, sodium acid pyrophosphate ($Na_2H_2P_2O_7$) may be present in an amount of from about 0.1% to about 5%, e.g., from about 0.1% to about 3%, from about 0.1% to about 2%, from about 0.1% to about 1%, from about 0.1% to about 0.5%, from about 0.2% to about 0.5%, from about 0.3% to about 0.5%, or about 0.4%, by weight of the oral care composition.

The oral care composition of the present invention may comprise a basic amino acid in free or salt form. The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrullene, ornithine, creatine, histidine, diaininobutanoic acid, diaminopropionic acid, salts thereof or combinations thereof. In a particular embodiment, the basic amino acids are selected from arginine, lysine, citrullene, and ornithine. The basic amino acids of the oral care composition may generally be present in the L-form or L-configuration. The basic amino acids may be provided as a salt of a di- or tri-peptide including the amino acid. In some embodiments, at least a portion of the basic amino acid present in the oral care composition is in the salt form. In some embodiments, the basic amino acid is arginine, for example, L-arginine, or a salt thereof. Arginine may be provided as free arginine or a salt thereof. For example, Arginine may be provided as arginine phosphate, arginine hydrochloride, arginine sulfate, arginine bicarbonate, or the like, and mixtures or combinations thereof. The basic amino acid may be provided as a solution or a solid. For example, the basic amino acid may be provided as an aqueous solution. In some embodiment, the amino acid includes or is provided by an arginine bicarbonate solution. For example, the amino acid may be provided by an about 40% solution of the basic amino acid, such as arginine bicarbonate or alternatively called as arginine carbamate. In some embodiments, the basic amino acid is present in an amount of from about 1% to about 15%, e.g., from about 1% to about 10%, from about 1% to about 5%, from about 1% to about 3%, from about 1% to about 2%, from about 1.2% to about 1.8%, from about 1.4% to about 1.6%, or about 1.5%, by weight of the oral care composition, being calculated as free base form.

The oral care composition of the present invention may comprise a zinc ion source. The zinc ion source may be or include a zinc ion and/or one or more zinc salts. For example, the zinc salts may at least partially dissociate in an aqueous solution to produce zinc ions. Illustrative zinc salts may include, but are not limited to, zinc lactate, zinc oxide, zinc chloride, zinc phosphate, zinc citrate, zinc acetate, zinc borate, zinc butyrate, zinc carbonate, zinc formate, zinc gluconate, zinc glycerate, zinc glycolate, zinc picolinate, zinc proprionate, zinc salicylate, zinc silicate, zinc stearate, zinc tartrate, zinc undecylenate, and mixtures thereof. In some embodiments, the zinc ion source is present in an amount of from about 0.01% to about 5 wt. %, e.g., about 0.1% to about 4 wt. %, or about 1% to about 3 wt. %, based on the total weight of the oral care composition.

The oral care composition of the present invention may include a stannous ion source. The stannous ion source can be a soluble or an insoluble compound of stannous with inorganic or organic counter ions. Examples include the fluoride, chloride, acetate, hexafluorozirconate, sulfate, tartrate, gluconate, citrate, malate, glycinate, pyrophosphate, metaphosphate, oxalate, phosphate, carbonate salts and oxides of stannous. In some embodiments, the stannous ion source is selected from the group consisting of stannous chloride, stannous fluoride, stannous pyrophosphate, stannous formate, stannous acetate, stannous gluconate, stannous lactate, stannous tartrate, stannous oxalate, stannous malonate, stannous citrate, stannous ethylene glycoxide, and mixtures thereof.

The oral care composition of the present invention may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

The oral care composition of the present invention may include one or more sweeteners safe for oral application. The sweetener may be, for example, saccharin, for example sodium saccharin, aspartame, acesulfame, neotame, cyclamate or sucralose; natural high-intensity sweeteners such as thaumatin, stevioside or glycyrrhizin; or such as sorbitol, xylitol, maltitol or mannitol. In certain embodiments, the sweetener is selected from sucralose, saccharin, aspartame, acesulfame, or a combination thereof. The one or more sweeteners may be present in an amount of from about 0.001% to about 2% by weight, for example about 0.001% to about 2, about 0.001% to about 1, about 0.001% to about 0.5, about 0.001% to about 0.08%, about 0.001% to about 0.05 wt. %, about 0.01% to about 0.05 wt. %, or about 0.04 to about 0.07 wt. %, based on the weight of the oral care composition. In a certain embodiment, the composition comprises a triple sweetener system of sodium Saccharin, Sucralose and rebaudioside M (Reb M). In certain preferred embodiments, the sweetener is sucralose and is present in an amount from about 0.01% to about 0.08%, by weight of the composition.

The oral care composition of the present invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 3%, about 0.01% to about 2, about 0.01% to about 1, about 0.01% to about 0.5, about 0.01% to about 0.08%, about 0.01% to about 0.05 wt. %, by weight based on the total weight of the oral care composition.

The oral care composition of the invention may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations and mixtures thereof.

The oral care composition of the invention may include one or more pigments, such as whitening pigments. In some embodiments, the whitening pigments include particles ranging in size from about 0.1 μm to about 10 μn with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxyapatite particles, calcium carbonate particles, zinc phosphate particles, silicon dioxide particles, zirconium silicate particles, or the like, or mixtures and combinations thereof. The whitening pigment, such as titanium dioxide particles, may be present in an amount that is sufficient to whiten the teeth.

All ingredients for use in the compositions described herein should be orally acceptable. As used herein, "orally acceptable" may refer any ingredient that is present in a composition as described in an amount and form which does not render the composition unsafe for use in the oral cavity.

In certain non-limiting embodiments, the oral care composition may comprise a formulation as specified in table 1, below.

TABLE 1

| Description | % |
|---|---|
| Cross-linked PVP complexed with Hydrogen peroxide | 0.550-36.000 |
| Sodium Monofluorophosphate | 0.00-1.140 |
| Sodium Fluoride | 0.00-0.320 |
| Potassium Nitrate | 0.00-5.000 |
| Polyethylene Glycol/Polypropylene Glycol-L1220 | 0.01-7.500 |
| SODIUM LAURYL SULFATE POWDER | 0.01-2.000 |
| SUCRALOSE USP, EP | 0.001-0.050 |
| Sodium Stearate ET | 0.01-5.000 |
| Flavor | 0-2.000 |
| Propylene Glycol USP, EP | q.s. |
| Total Components | 100.000 |

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure.

Example 1

A whitening toothpaste serum composition having the formulation as described in Table 2 (below) was prepared.

TABLE 2

| Ingredient | Wt. % |
|---|---|
| Cross-linked PVP complexed with Hydrogen peroxide | 22.000 |
| Polyethylene Glycol/Polypropylene Glycol-L1220 | 7.500 |
| Sodium Lauryl Sulfate | 1.000 |
| Sucralose | 0.050 |
| Sodium Stearate | 0.500 |
| Propylene Glycol | q.s. (68.95) |
| Total Components | 100.000 |

The composition described in Table 2 (above) yields 4% hydrogen peroxide, as delivered from the cross-linked PVP complexed with hydrogen peroxide.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. An oral care composition comprising:
   a whitening complex present in an amount to provide from about 3% to about 8% of hydrogen peroxide, by weight of the oral care composition;
   a block copolymer of ethylene oxide and propylene oxide in an amount from about 0.01% to about 8% by weight of the oral care composition;
   a stearate in an amount from about 0.3% to about 5%, by weight of the composition, wherein the stearate is selected from sodium stearate, potassium stearate, calcium stearate, and a combination thereof; and
   a humectant in an amount from about 60% to about 90% by weight of the oral care composition.

2. The oral care composition according to claim 1, wherein the humectant consists of sorbitol, polyethylene glycol, propylene glycol, xylitol, or a combination of two or more thereof.

3. The oral care composition according to claim 1, wherein the whitening complex comprises a crosslinked polyvinylpyrrolidone complexed with hydrogen peroxide (PVP-$H_2O_2$).

4. The oral care composition according to claim 1, wherein the whitening complex is present in an amount to provide from about 3.5% to about 4.5% of hydrogen peroxide, by weight of the oral care composition.

5. The oral care composition according to claim 1, wherein the block copolymer of ethylene oxide and propylene oxide is present in an amount from about 5% to about 7.5%, by weight of the oral care composition.

6. The oral care composition according to claim 1, wherein the stearate is present in an amount from about 0.3% to about 0.8%, by weight of the oral care composition.

7. The oral care composition according to claim 1, wherein the stearate consists of sodium stearate, potassium stearate, calcium stearate or a combination thereof.

8. The oral care composition according to claim 1, wherein the humectant comprises from about 60% to about 80%, by weight of the composition, of propylene glycol.

9. The oral care composition according to claim 1, wherein the composition further comprises sucralose in an amount from about 0.01% to about 2%, by weight of the composition.

10. The oral care composition according to claim 1, wherein the composition further comprises an anionic surfactant selected from: sodium lauryl sulfate; sodium laureth sulfate; sodium alkyl benzene sulfonate; sodium lauroyl sarcosinate; sodium N-methyl-N-cocoyl taurate; sodium cocomoglyceride sulfate; sodium lauryl sulfoacetate; and a combination of two or more thereof.

11. The oral care composition according to claim 10, wherein the anionic surfactant is present in an amount from about 0.01% to about 2%, by weight of the composition, optionally from about 0.5% to about 1%, by weight of the composition.

12. The oral care composition according to claim 1, wherein the oral care composition is free or substantially free of an abrasive.

13. The oral care composition according to claim 1, wherein the oral care composition is free or substantially free of water.

14. A method of whitening teeth, comprising mixing the oral care composition according to claim 1 with a toothpaste, and applying the mixed composition to a tooth surface.

15. The method according to claim 14, wherein the mixing is performed at an oral care composition to toothpaste mass ratio of about 1:1 to about 1:4.

16. The method according to claim 15, wherein the mixed composition has a weight ratio of the oral care composition to toothpaste mass ratio of about 1:1 to about 1:4.

17. An oral care composition consisting essentially of:
- a crosslinked polyvinylpyrrolidone complexed with hydrogen peroxide (PVP-$H_2O_2$) present in an amount to provide from about 3% to about 8% of hydrogen peroxide, by weight of the oral care composition;
- a block copolymer of ethylene oxide and propylene oxide in an amount from about 0.01% to about 8%, by weight of the oral care composition;
- a stearate in an amount from about 0.3% to about 1%, by weight of the oral care composition, wherein the stearate is selected from sodium stearate, potassium stearate, calcium stearate, and a combination thereof;
- propylene glycol in an amount from about 60% to about 90%, by weight of the oral care composition;
- sodium lauryl sulfate present in an amount from about 0.01% to about 2.0%, by weight of the oral care composition; and
- sucralose present in an amount from about 0.01% to about 2%, by weight of the oral care composition.

18. A method of whitening teeth, comprising applying an oral care composition according to claim 17 to a tooth surface.

19. An oral care composition comprising:
- a crosslinked polyvinylpyrrolidone complexed with hydrogen peroxide (PVP-$H_2O_2$) present in an amount to provide from about 3% to about 8% of hydrogen peroxide, by weight of the oral care composition;
- a block copolymer of ethylene oxide and propylene oxide in an amount from about 0.01% to about 8%, by weight of the oral care composition;
- a stearate in an amount from about 0.3% to about 1%, by weight of the oral care composition, wherein the stearate is selected from sodium stearate, potassium stearate, calcium stearate, and a combination thereof;
- propylene glycol in an amount from about 60% to about 90%, by weight of the oral care composition;
- sodium lauryl sulfate present in an amount from about 0.01% to about 2.0%, by weight of the oral care composition; and
- sucralose present in an amount from about 0.01% to about 2%, by weight of the oral care composition.

20. An oral care kit comprising:
- a container;
- the oral care composition according to claim 1, the oral care composition being disposed in the container; and
- optionally, a toothpaste disposed in the container.

* * * * *